United States Patent
Bonrath et al.

(10) Patent No.: US 9,902,674 B2
(45) Date of Patent: Feb. 27, 2018

(54) PROCESS OF PRODUCTION OF 2,5-DIMETHYLPHENOL

(71) Applicant: DSM IP ASSETS B.V., Heerlen (NL)

(72) Inventors: Werner Bonrath, Kaiseraugst (CH); Ulla Letinois, Kaiseraugst (CH); Thomas Netscher, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/114,144

(22) PCT Filed: Jan. 27, 2015

(86) PCT No.: PCT/EP2015/051601
§ 371 (c)(1),
(2) Date: Jul. 26, 2016

(87) PCT Pub. No.: WO2015/110655
PCT Pub. Date: Jul. 30, 2015

(65) Prior Publication Data
US 2017/0001935 A1 Jan. 5, 2017

(30) Foreign Application Priority Data
Jan. 27, 2014 (EP) .................................. 14152707

(51) Int. Cl.
*C07C 37/14* (2006.01)
*B01J 31/24* (2006.01)

(52) U.S. Cl.
CPC ........... *C07C 37/14* (2013.01); *B01J 31/2404* (2013.01); *B01J 2231/48* (2013.01); *B01J 2531/18* (2013.01)

(58) Field of Classification Search
None
See application file for complete search history.

(56) References Cited

PUBLICATIONS

International Search Report for PCT/EP2015/051601 dated Apr. 7, 2015, two pages.
Written Opinion of the ISA for PCT/EP2015/051601 dated Apr. 7, 2015, six pages.
K. Anderson et al., "The Selective Reaction of Aryl Halides with KOH: Synthesis of Phenols, Aromatic Ethers, and Benzofuransa", *Journal of the American Chemical Society*, American Chemical Society, vol. 128, No. 33, Jan. 1, 2006, pp. 10694-10695.
Khouw et al., "Studies of the Catalytic-Oxidation of Alkanes and Alkenes by Titanium Silicates", *Journal of Catalysis*, vol. 149, No. 1, Sep. 1, 1994, pp. 195-205.
Huguet et al; Intermolecular Gold(I)-Catalyzed Cyclization of Furans with Aklynes: Formation of Phenols and Indenes, *Chem. Eur. J.*, 2013, 19, 6581-6585.

*Primary Examiner* — Rosalynd A Keys
(74) *Attorney, Agent, or Firm* — Nixon & Vanderhye P.C.

(57) ABSTRACT

The present invention relates to a new method to produce 2,5-dimethylphenol (2,5-DMP).

8 Claims, No Drawings

PROCESS OF PRODUCTION OF 2,5-DIMETHYLPHENOL

This application is the U.S. national phase of International Application No. PCT/EP2015/051601 filed 27 Jan. 2015 which designated the U.S. and claims priority to EP Patent Application No. 14152707.7 filed 27 Jan. 2014, the entire contents of each of which are hereby incorporated by reference.

The present invention relates to a new method to produce 2,5-dimethylphenol (2,5-DMP).

2,5-dimethylphenol, which is also called 2,5 xylenol, can be used for example as an intermediate in the production of vitamin E.

Xylenols are organic compounds with the formula (I)

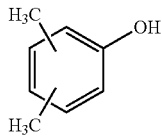

(I)

They are volatile colorless solids or oily liquids. They are derivatives of phenol with two methyl groups and a hydroxyl group. Six isomers are existing.

Together with many other compounds, xylenols are traditionally extracted from coal tar, the volatile materials obtained in the production of coke from coal. These residues contain a few percent by weight of xylenols as well as cresols and phenol.

Together with cresols and cresylic acid, xylenols are an important class of phenolics with great industrial importance. They are used in the manufacture of antioxidants. Xylenol orange is a redox indicator built on a xylenol skeleton.

2,5-DMP, which is the compound of formula (Ia)

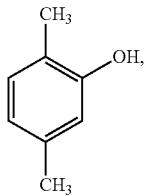

(Ia)

is an intermediate in the production of the 2,3,6-trimethylphenol (2,3,6-TMP) which is the compound of formula (II)

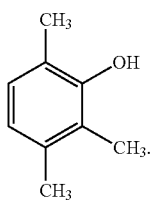

(II)

2,3,6-TMP is usually produced by a gasphase methylation of 2,5-DMP.

2,3,6-TMP can be used as such (for example in cosmetic formulations) as well as intermediate in the production of other organic compounds, such as for example vitamin E.

Due to fact that of 2,5-DMP is obtained from not renewable resources, an alternative, more sustainable production of 2,5-DMP is desirable.

We now found a new way for the production of 2,5-DMP, which is carried out by using a starting material, which is obtained from a renewable source (cellulose).

We found that 2,5-dimethylfuran can be used as a starting material, which is then reacted with ethyne and/or an ethyne-derivative.

2,5-dimethylfuran, which is the compound of formula (III)

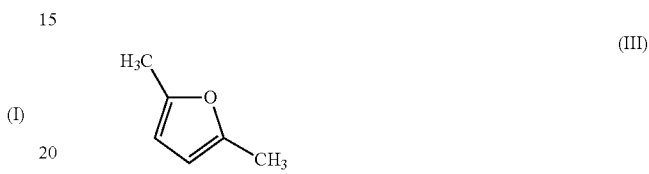

(III)

is a heterocyclic compound which is derivable from cellulose.

This process is known from the prior art (i.e. Y. Román-Leshkov, C. J. Barrett, Z. Y. Liu, J. A. Dumesic, Nature 2007, 447, 982-985).

It is known that fructose can be converted into 2,5-dimethylfuran in a catalytic biomass-to-liquid process.

Fructose is obtainable from glucose, a building block in cellulose.

Therefore the present invention is related to the following process (A):

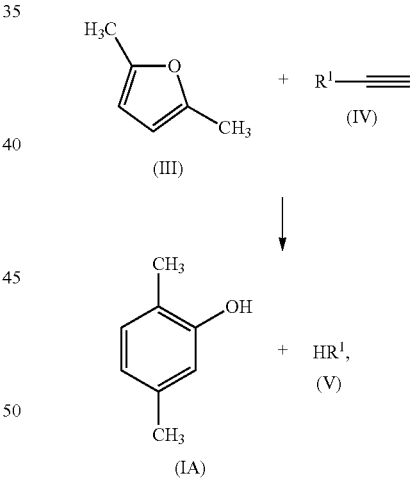

wherein $R^1$ is H or $Si(CH_3)_3$,
in the presence of a catalyst.

Preferably the catalyst used in the processes as described above the catalyst is an Au(I) complex.

Therefore the present invention also relates to process (B), which process (A), wherein the catalyst is an Au(I) complex.

Especially the following Au(I)-complexes are used as catalysts for the process according to the present invention:

$$Y\text{—}Au(I)\text{—}Z \quad (VI),$$

wherein
Z is an anion, which is selected from the group consisting of $[BX_4]^-$, $[PX_6]^-$, $[SbF_6]^-$, $[ClO_4]^-$, $CF_3COO^-$, sulfonates, tetra(3,5-bis(trifluoromethyl)phenyl)borate (BAr$_F^-$), tetraphenylborate, and the following anion of formula (VII)

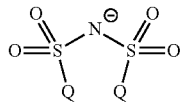

(VII)

wherein Q represents a phenyl or a $C_{1-8}$-alkyl which preferably is substituted by at least one substituent chosen from the group consisting of F, Cl and $NO_2$, and X is a halogen atom, especially F and Cl, and Y is an organic ligand.

Therefore the present invention also relates to process (C), which is the process (A) or (B), wherein at least one Au(I) complex of the following compound of formula (VI) is used Y—Au(I)—Z  (VI), wherein Z is an anion, which is selected from the group consisting of $[BX_4]^-$, $[PX_6]^-$, $[SbF_6]^-$, $[ClO_4]^-$, $CF_3COO^-$, sulfonates, tetra(3,5-bis(trifluoromethyl)phenyl)borate (BAr$_F^-$), tetraphenylborate, and the following anion of formula (VII)

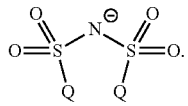

(VII)

wherein Q represents a phenyl or a $C_{1-8}$-alkyl group, which preferably is substituted by at least one substituent chosen from the group consisting of F, Cl and $NO_2$, and X is a halogen atom, especially F and Cl, and Y is an organic ligand.

Preferably Y is an organic ligand selected from the group consisting of following ligands ($Y^1$) to ($Y^{10}$):

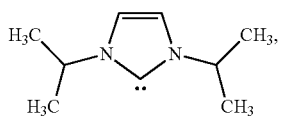

($Y^1$)

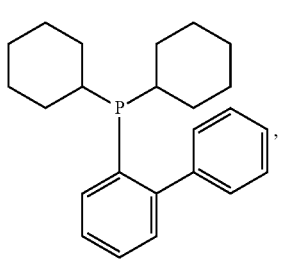

($Y^2$)

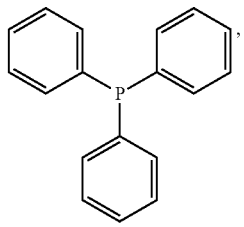

($Y^3$)

($Y^4$)

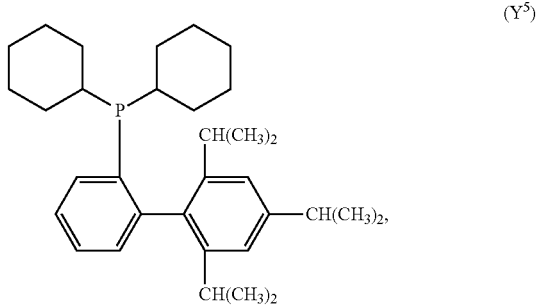

($Y^5$)

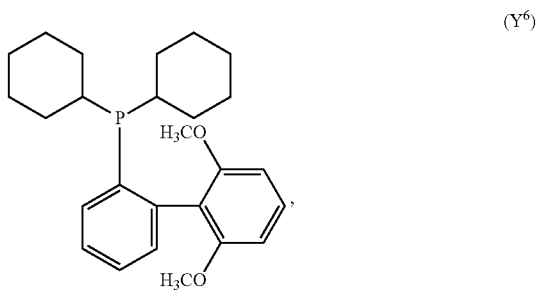

($Y^6$)

($Y^7$)

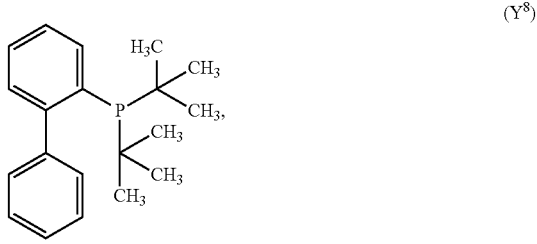

($Y^8$)

(Y⁹)

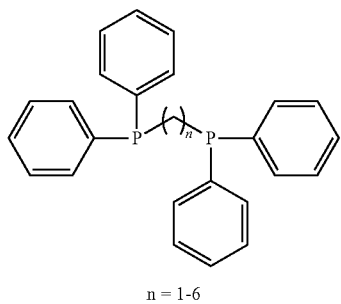

n = 1-6

(Y¹⁰)

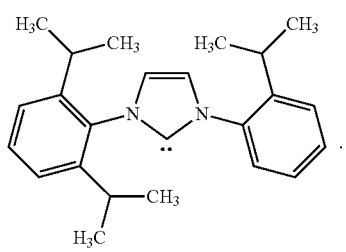

Therefore the present invention also relates to process (C'), which is the process (C), wherein the organic ligand Y of Au(I) complex of formula (VI) is selected from the group consisting of following ligands (Y¹) to (Y¹⁰):

(Y¹)

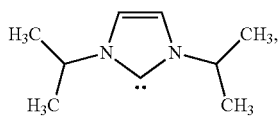

(Y²)

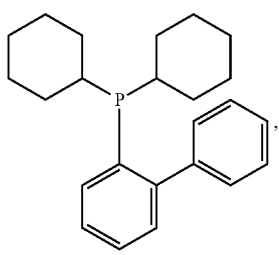

(Y³)

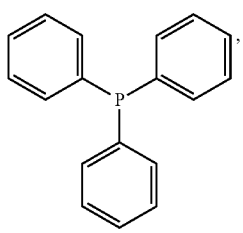

(Y⁴)

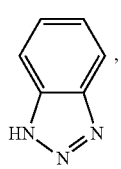

(Y⁵)

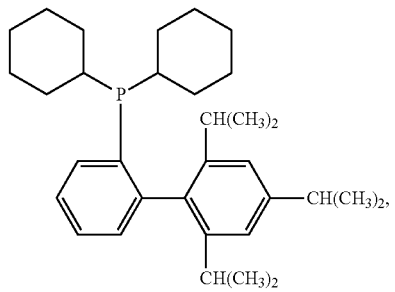

(Y⁶)

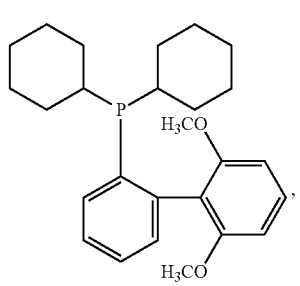

(Y⁸)

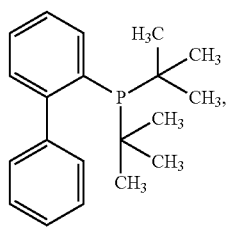

(Y⁹)

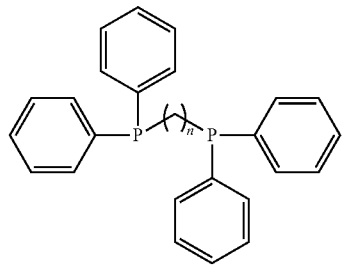

n = 1-6

(Y¹⁰)

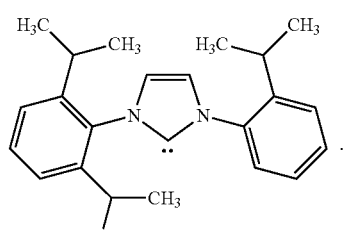

Preferably Z is an anion selected from the group consisting of following anions [BF₄]⁻, [PF₆]⁻, [SbF₆]⁻, [ClO₄]⁻, CF₃COO⁻, sulfonates (such as triflate CF₃SO₃⁻), tetra(3,5-bis(trifluoromethyl)phenyl)borate (BAr$_F$⁻), tetraphenylborate, and the following anion of formula (VII')

(VII')

[Structure: bis(trifluoromethylsulfonyl)imide anion]

Therefore the present invention also relates to process (C"), which is the process (C) or (C'), wherein the anion Z is selected from the group consisting of following anions $[BF_4]^-$, $[PF_6]^-$, $[SbF_6]^-$, $[ClO_4]^-$, $CF_3COO^-$, sulfonates, tetra(3,5-bis(trifluoromethyl)phenyl)borate ($BAr_F^-$), tetraphenylborate, and the following anion of formula (VII')

(VII')

[Structure: bis(trifluoromethylsulfonyl)imide anion]

The catalyst (the Au(I) complex) can be added to the reaction mixture in the form, which is defined by formula (I), but it is also possible that the Au(I)-complex is formed in situ in the reaction mixture (before the starting material is added or after the starting material is added).

For example it is possible to add the organic ligand in the form of a salt (such as for example a chloride: Y—Au(I)Cl) and the anion in form of a metal salt (such for example a silver salt Ag(I)Z). The Au(I) complex is then formed in situ and the resulting metal salt (for example AgCl) does not interfere negatively.

Therefore the present invention relates to a process (D), which is the process (C), (C') or (C"), wherein the Au(I) complex is added to reaction mixture as such.

Furthermore the present invention relates to a process (E), which is the process (C), (C') or (C"), wherein the Au(I) complex is formed in situ in the reaction mixture.

Preferred Au(I) complexes of formula (V) are the following one.

(V')

[Structure: JohnPhos-type Au complex with $F_6SbAu$]

(V")

[Structure: biphenyl phosphine Au-NTf$_2$ complex with (Cy)$_2$P and OMe groups] and (V''')

[Structure: biphenyl phosphine SbF$_6$ complex with Cy and iPr groups]

wherein Cy is cyclohexyl, iPr is isopropyl and Tf is triflate.

When a propyne derivate is used (instead of propyne), then $R^1$ is chosen in a way that this derivative is easier handable than propyne and wherein $R^1$ is forming a reaction product which can be removed easily from the reaction mixture.

In the case of $R_1$=Si(CH$_3$)$_3$, then the compound of formula (III) is liquid. Therefore it is also possible to use other propyne derivatives than the one with the Si(CH$_3$)$_3$ group, when they have the properties as described above.

Usually the Au(I) complex is present in an amount, wherein the substrate (compound of formula (I)) to catalyst ratio is 2:1 to 10000:1, preferred are 10:1 to 3000:1. The ratio is weight based.

Therefore the present invention also relates to a process (F), which is the process (A), (B), (C), (C'), (C"), (D) or (E), wherein the substrate to catalyst ratio is 2:1 to 10000:1, preferred are 10:1 to 3000:1.

A further embodiment is the process according to the present invention wherein benzonitrile is added to the reaction mixture at the start of the process. Usually it is added in an equimolar amount in regard to the catalyst.

Therefore the present invention also relates to a process (G), which is the process (A), (B), (C), (C'), (C"), (D), (E) or (F), wherein benzonitrile is added to the reaction mixture.

Therefore the present invention also relates to a process (G'), which is the process (G), wherein benzonitrile is added to the reaction mixture in an equimolar amount in regard to the catalyst.

The process according to the present invention is usually carried out under normal pressure.

Therefore the present invention also relates to a process (H), which is the process (A), (B), (C), (C'), (C"), (D), (E), (F), (G) or (G'), wherein the process is carried out under normal pressure.

The reaction temperature of the process according to the present invention is usually between 10-50° C. Preferably between 15-30° C.

Therefore the present invention also relates to a process (I), which is the process (A), (B), (C), (C'), (C"), (D), (E), (F), (G), (G') or (H), wherein the process is carried out between 10-50° C., preferably between 15-30° C.

The reaction is usually carried out in an inert solvent (or mixture of solvents). Preferably the solvent (or the mixture of solvents) has a neutral or acidic pH value. Preferred solvents are dichloromethane, 1,2-dichloroethane, trifluoroethanol, chloroform, toluene, ethyl acetate, cyclohexanone, acetone.

More preferred are dichloromethane, trifluoroethanol and 1,2-dichloroethane as well as a mixture of dichloromethane with 5 vol % of trifluoroethanol.

Furthermore it is also possible to use an ionic liquid as a solvent. Very suitable ionic liquids are the following ones (IL$^1$, IL$^2$ and IL$^3$):

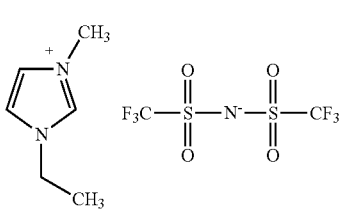
(IL¹)

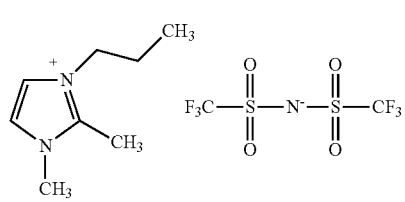
(IL²)

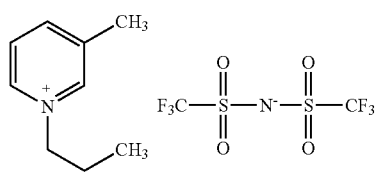
(IL³)

Therefore the present invention also relates to a process (K), which is the process (A), (B), (C), (C'), (C"), (D), (E), (F), (G), (G'), (H) or (I), wherein the process is carried in an inert solvent (or mixture of solvents).

Therefore the present invention also relates to a process (K'), which is the process (K), wherein the solvent (or the mixture of solvents) has a neutral or acidic pH value.

Therefore the present invention also relates to a process (K"), which is the process (K) or (K'), wherein the solvent is chosen from the group consisting of dichloromethane, 1,2-dichloroethane, trifluoroethanol, chloroform, toluene, ethyl acetate, cyclohexanone, acetone.

Therefore the present invention also relates to a process (K'") which is the process (K), (K') or (K"), wherein the solvent is chosen from the group consisting of dichloromethane, trifluoroethanol and 1,2-dichloroethane as well as a mixture of dichloromethane with 5 vol % of trifluoroethanol.

Therefore the present invention also relates to a process (K""), which is the process (K), (K') or (K"), wherein the solvent is an ionic liquid (or a mixture of ionic liquis).

Therefore the present invention also relates to a process (K'""), which is the process (K""), wherein the ionic liquids are those of formula (IL¹), (IL²) and/or (IL³).

The following examples serve to illustrate the invention. All percentages and parts (if not otherwise stated) are related to the weight and the temperature is given in ° C.

EXAMPLES

Example 1

To a 2 mL glass bottle, fitted with a septum, a magnetic stirring bar and argon supply are added 34.55 mg of the compound of the following formula

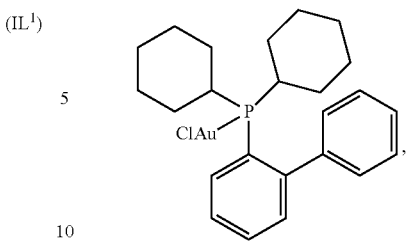

which is $Y^2$—Au(I)Cl, 30.66 mg AgSbF$_6$ and 500 µL 2,5-dimethylfuran and suspended in 1 mL dichloromethane. Then 144.2 µL trimethylsilylacetylene was added b syringe. The reaction mixture was stirred for 20 hours at 40° C. A sample was taken out by syringe and analysed. 2,5-Dimethylphenol was obtained in 17% yield relative to 2,5-dimethylfuran (GC wt %).

Example 2

A three-necked round bottom flask, fitted with argon supply, a thermometer and a magnetic stirring bar was charged with 121.3 mg of $Y^2$—Au(I)Cl (200 µmol, 2 mol %), 99.5 mg AgSbF$_6$ (200 µmol, 2 mol %) and 10 mL of 1,2-dichloroethane. A previously prepared solution of 240 mg acetylene (10 mmol, 1 equiv.), 1.07 mL 2,5-dimethylfuran (10 mmol 1 equiv.) in 22 mL 1,2-dichloroethane was added dropwise over a period of 30 minutes. The reaction mixture, which changes its colour to red and violet over the addition time is kept at 20° C. inner temperature by using an external cooling device (ice-bath). The reaction mixture is stirred for 20 hours at 23° C. Then the saturated acetylene/1,2-dichloroethane solution is added three times with a time-lag of 1 hour. The reaction mixture is again stirred for 20 hours at 23° C. The reaction mixture is concentrated under reduced pressure (min. 10 mbar, 40° C.). The black liquid is dissolved in 30 mL ethyl acetate and 5 mL cyclohexane are added. The solution is left standing at 23° C. for 8 hours. Dark crystals containing the catalyst have formed which are filtered off. The supernatant is concentrated under reduced pressure and analyzed. The desired product was obtained in 20% yield based on dimethylfuran. 2,5-dimethylphenol can be conveniently transferred to 2,3,6-trimethylphenol by state of the art gas phase methylation.

The invention claimed is:

1. A process for producing a compound of formula (Ia):

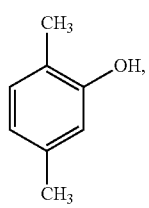
(Ia)

wherein
the process comprises reacting a the compound of formula (III):

with a compound of formula (IV):

R¹—≡—, (IV)

wherein R¹ is H or Si(CH₃)₃,
in the presence of a catalyst which comprises at least one Au(I) complex of formula (VI):

Y—Au(I)—Z (VI), wherein

Z is an anion, which is selected from the group consisting of [BX₄]⁻, [PX₆]⁻,
[SbF₆]⁻, [ClO₄]⁻, CF₃COO⁻, sulfonates, tetra(3,5-bis(trifluoromethyl)phenyl)borate (BAr$_F^-$), tetraphenylborate, and an anion of formula (VII):

(VII)

wherein
Q represents a phenyl or a C₁₋₈-alkyl,
X is a halogen atom, and
Y is an organic ligand selected from the group consisting of ligands (Y¹) to (Y¹⁰):

(Y¹) — (Y¹⁰) structures shown n = 1-6

-continued

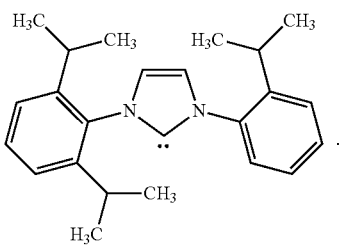

(Y¹⁰)

2. The process according to claim 1, wherein Z is an anion selected from the group of ions consisting of $[BF_4]^-$, $[PF_4]^-$, $[SbF_6]^-$, $[ClO_4]^-$, $CF_3COO^-$, sulfonate, tetra(3,5-bis(trifluoromethyl)phenyl)borate ($BAr_F^-$), tetraphenylborate, and an anion of formula (VII')

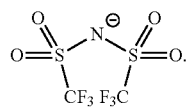

(VII')

3. The process according to claim 1, wherein the process comprises adding the Au(I) complex to a reaction mixture comprising the compounds of formulas (III) and (IV).

4. The process according to claim 1, wherein the Au(I) complex is formed in situ in a reaction mixture comprising the compounds of formulas (III) and (IV).

5. The process according to claim 1, wherein the Au(I) complex has a substrate to catalyst ratio which is 2:1 to 10000:1.

6. The process according to claim 5, wherein the substrate to catalyst ratio is 10:1 to 3000:1.

7. The process according to claim 1, wherein Q represents a phenyl or a $C_{1-8}$-alkyl which is substituted by at least one substituent selected from the group consisting of F, Cl and $NO_2$.

8. The process according to claim 1, wherein X is F or Cl.

* * * * *